United States Patent
Wilson et al.

(10) Patent No.: US 11,826,371 B2
(45) Date of Patent: Nov. 28, 2023

(54) ORAL FORMULATION OF CLONIDINE AND MIDAZOLAM FOR SEDATION IN DENTAL PROCEDURES

(71) Applicant: Transdermal Sedation Solutions, LLC, Little Rock, AR (US)

(72) Inventors: Pamala Lea Wilson, Owasso, OK (US); James Liddell McCarley, Little Rock, AR (US)

(73) Assignee: Therapeutic Sedation Solutions, LLC, Rogers, AR (US)

( * ) Notice: Subject to any disclaimer, the term of this patent is extended or adjusted under 35 U.S.C. 154(b) by 0 days.

(21) Appl. No.: 17/542,651

(22) Filed: Dec. 6, 2021

(65) Prior Publication Data
US 2022/0175794 A1 Jun. 9, 2022

Related U.S. Application Data

(60) Provisional application No. 63/121,939, filed on Dec. 6, 2020, provisional application No. 63/217,189, filed on Jun. 30, 2021.

(51) Int. Cl.
| | |
|---|---|
| A61K 31/4168 | (2006.01) |
| A61K 31/4468 | (2006.01) |
| A61K 31/5517 | (2006.01) |
| A61P 23/00 | (2006.01) |
| C07D 487/04 | (2006.01) |
| C07D 233/50 | (2006.01) |
| C07D 211/58 | (2006.01) |
| A61K 9/00 | (2006.01) |

(52) U.S. Cl.
CPC ........ *A61K 31/5517* (2013.01); *A61K 9/0056* (2013.01); *A61K 31/4168* (2013.01); *A61K 31/4468* (2013.01); *A61P 23/00* (2018.01)

(58) Field of Classification Search
CPC ............ A61K 31/4168; A61K 31/4468; A61K 31/5517; A61K 9/0056; A61P 23/00; C07D 487/04; C07D 233/50; C07D 211/58
See application file for complete search history.

(56) References Cited

PUBLICATIONS

Trevor et al, "A comparison of midazolam and clonidine as an oral premedicationin pediatric patients" (2012) *Saudi J Anaesth*. 6(1):8-11.
Salem et al, "Two Oral Midazolam Preparations in Pediatric Dental Patients: A Prospective Randomised Clinical Trial" (2015) *International Journal of Pediatrics*, article ID 349795.
International Search Report by the USPTO dated Feb. 23, 2022, for PCT/US21/61960.
Written Opinion by the USPTO dated Feb. 23, 2022, for PCT/US21/61960.

*Primary Examiner* — Brenda L Coleman
(74) *Attorney, Agent, or Firm* — Ryuh Patent Law; Steven Yu

(57) ABSTRACT

A drug composition in solid drug matrix formulation comprising clonidine, midazolam, and fentanyl. The amounts of the drug contained in the solid drug matrix are sufficient to induce sedation in preparation for a clinical procedure. When administered in the mouth, the drug ingredients are absorbed by transmucosal passage. This solid drug matrix formulation may be particularly useful in pediatric dentistry practice. Also disclosed is a method of inducing sedation in a patient by administering the solid drug matrix formulation to the patient prior to performing a clinical procedure.

20 Claims, 1 Drawing Sheet

FIG. 1
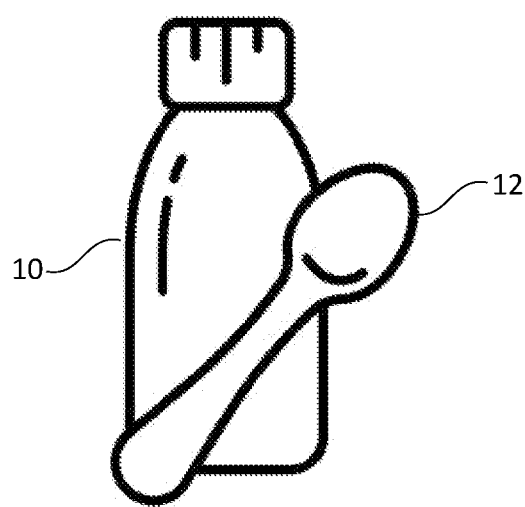
FIG. 2
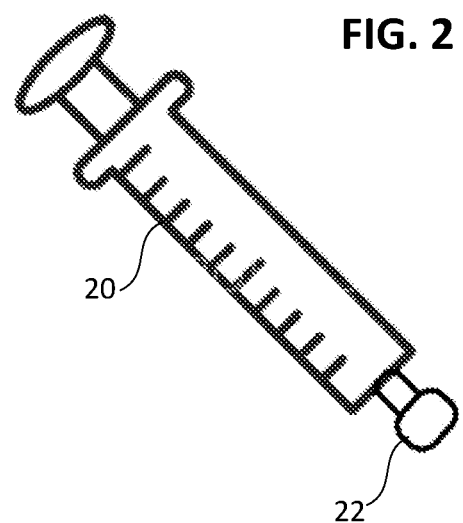
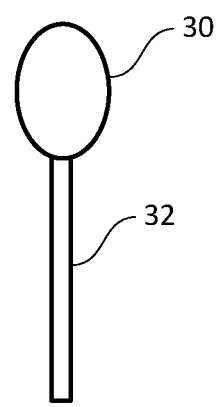
FIG. 3
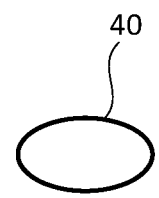
FIG. 4

ORAL FORMULATION OF CLONIDINE AND MIDAZOLAM FOR SEDATION IN DENTAL PROCEDURES

TECHNICAL FIELD

The present invention relates to inducing sedation in patients for performing a dental procedure.

BACKGROUND

In dental care practice, fear and anxiety are common problems in pediatric patients. The dental practitioner can use many techniques to manage this problem. In particular, various sedation techniques using anesthetic agents are being more widely used. The field of pediatric dentistry has been greatly improved by office-based anesthesia to help increase children's access to dental care. This is done by providing anesthesia services in the office rather than a hospital setting. This allows the child to be treated in a less stressful environment. Also, by avoiding the need for hospital scheduling, it reduces the wait time for treatment of their dental needs.

In-office sedation is still a developing practice. The goals of sedation in the pediatric patient for diagnostic and therapeutic procedures are as follows: (1) to guard the patient's safety and welfare; (2) to minimize physical discomfort and pain; (3) to control anxiety, minimize psychological trauma, and maximize the potential for amnesia; (4) to modify behavior or movement to allow safe completion of the procedure; and (5) to return the patient to a state in which discharge from medical supervision is safe. All these factors must be managed to deliver predictable, safe, and reliably effective conscious sedation in pediatric dentistry. There is a continuing need for an efficacious manner of inducing conscious sedation in patients for performing dental procedures, particularly in children.

SUMMARY

In general, this invention relates to a composition comprising a mixture of a benzodiazepine and clonidine, and optionally other drug ingredients. This allows the two active ingredients to be given simultaneously for inducing sedation in a patient. This sedation is done in preparation for performing a clinical procedure on the patient. There are a variety of different types of benzodiazepines that could be used in this invention. The most common benzodiazepine used in this setting is midazolam because it has a short duration of action. The composition could further comprise an opioid drug. Examples of opioid drugs that could be used include fentanyl, sufentanil, and meperidine.

LIQUID COMPOSITION: In one aspect, the invention is a liquid composition comprising a mixture of clonidine and a benzodiazepine. The composition is a liquid and may have the form of any of the various types of liquid mixtures, such as a syrup, elixir, solution, suspension, emulsion, etc. The liquid composition comprises clonidine and a benzodiazepine (e.g. midazolam) in combination at amounts sufficient to induce sedation.

The following are possible drug concentrations amounts contained in the liquid composition. Clonidine. In some embodiments, the amount of clonidine contained therein is in the range of 5.0-50 µg/ml; and in some cases, 8.0-35 µg/ml. Midazolam. In some embodiments, the amount of midazolam contained therein is in the range of 0.5-10 mg/ml; and in some cases, 0.8-6.0 mg/ml. Fentanyl. The liquid composition could also comprise fentanyl as the opioid drug. In some embodiments, the liquid composition contains fentanyl in an amount in the range of 5-70 µg/ml; and in some cases, 15-50 µg/ml. Meperidine. The liquid composition could also comprise meperidine as the opioid drug. In some embodiments, the liquid composition contains meperidine in an amount in the range of 10-25 mg/ml; and in some cases, 2.0-10 mg/ml. Hydroxyzine. The liquid composition could also comprise an antihistamine. Examples of antihistamines include diphenhydramine and hydroxyzine. In some embodiments, the liquid composition contains hydroxyzine in an amount in the range of 1.0-40 mg/ml; and in some cases, 2.0-25 mg/ml.

In addition to the drug ingredients, the liquid composition could also contain other excipient ingredients, such as sweeteners (e.g. sugar or honey) and flavor enhancers (e.g. grape, cherry, bubblegum, strawberry, etc.). In some embodiments, the liquid composition contains no other sedative agent than the clonidine and the benzodiazepine. That is, the only sedative agents in the liquid composition are the clonidine and the benzodiazepine. In some embodiments, the liquid composition does not contain any opioid drug.

The liquid composition could be administered orally in any suitable manner. For example, the liquid could be administered by a drinking cup, spoon, syringe, or medicine dropper. The dose volume of the liquid composition is less than 15 ml. In some embodiments, the dose volume is less than 12 ml volume; and in some cases, less than 7 ml.

The liquid composition may be provided in aggregate multi-use volume. For example, a large bottle containing the liquid composition may be provided and the clinician draws up the appropriate amount for a particular patient from a fresh syringe, medication dropper, or medication spoon. In some embodiments, the invention is a container (e.g. plastic bottle) containing 25-400 ml of the liquid composition.

Alternatively, the liquid composition could be provided in convenient single-use format, which is intended to be sufficient for treating a single patient and any remaining amount is disposed. For example, a single dose of the liquid composition could be provided in a pre-filled syringe. In some embodiments, the invention is a single-use medication dispenser (e.g. small vial, pre-filled dropper, or pre-filled syringe) containing 2.0-20 ml of the liquid composition; and in some cases, 2.0-15 ml of the liquid composition.

SOLID DOSAGE FORM: In another aspect, the composition is a solid drug matrix formulation for transmucosal absorption in the mouth as the primary mode of drug delivery. This solid formulation is designed to be held in the mouth for at least a short duration (e.g. at least 5 seconds, such as for a rapidly disintegrating tablet or film), and could be for an extended duration (e.g. at least 3 minutes, such as for a lollipop). This is not intended to be swallowed in whole (although it may be swallowed after size shrinkage or fragmentation). There are various types of solid drug matrix dosage forms, such as lollipops, disintegrating tablets, disintegrating films, lozenge, troches, etc.

The solid drug matrix comprises clonidine and a benzodiazepine (e.g. midazolam), and optionally other drug ingredients, in combination at amounts sufficient to induce sedation. The following are possible drug amounts contained in the solid drug matrix formulation. Clonidine. In some embodiments, the amount of clonidine contained therein ranges from 10-300 µg; and in some cases, 30-180 µg. Midazolam. In some embodiments, the amount of midazolam therein ranges from 2-80 mg; and in some cases, 5-40 mg. Fentanyl. The solid drug matrix could also contain fentanyl as the opioid drug. In some embodiments, the amount of fentanyl therein ranges from 25-300 µg; and in some cases, 40-195 mg.

Limited Amount of Fentanyl. Limiting the amount of fentanyl may be useful in reducing the risk of respiratory depression and other unpleasant side effects of opioid drugs (e.g. nausea and vomiting). Because the drug composition also works synergistically with midazolam and clonidine, inducing sufficient sedation while using less fentanyl may be feasible. In some embodiments, the amount of fentanyl is less than 190 µg; in some cases, less than 175 µg; and in some cases, less than 150 µg. Note that the amounts of fentanyl given herein means the amount of the fentanyl moiety by itself (free base), without the mass of any corresponding salt or counterion. The molecular weight of the free base is 337 and the citrate salt is 529. Thus, for example, 100 mg of fentanyl citrate would give 64 mg of fentanyl (as base equivalent). In contrast, for the other drugs indicated herein, the amounts are expressed as the total mass of the compound (e.g. the amount of midazolam means the mass of midazolam HCl or other salt form used in making the drug composition).

Meperidine. The solid drug matrix could also contain meperidine as the opiate drug. In some embodiments, the amount of meperidine contained therein ranges from 10-400 mg; and in some cases, 15-250 mg. Hydroxyzine. The solid drug matrix could also comprise hydroxyzine. In some embodiments, the amount of hydroxyzine contained therein ranges from 10-180 mg; and in some cases, 15-100 mg.

Because the solid oral dosage form is not intended to be swallowed whole, it may be larger in size than typical tablets or capsules. In some embodiments, the size of the solid oral dosage form is at least 1.0 cm along its widest dimension; and in some cases, at least 1.5 cm. For example, in the case of a lollipop, this dimension may be the diameter of a spherical shape or the diameter of a disk shape. In another example, in the case of a lozenge, this dimension may be the length of an egg-shaped lozenge or the diameter of a doughnut-shaped lozenge. The solid oral dosage form should not be too large. In some cases, the size of the solid oral dosage form along its widest dimension is less than 3.5 cm.

The solid dosage form could have other excipients ingredients, such as flavor enhancers, sweeteners, etc. The oral dosage form should be sufficiently large to contain all the drug ingredients and the additional excipients (e.g. enough to mask the bitter taste). However, it should also be small enough to allow relatively quick disintegration in the patient's mouth. In some embodiments, the total weight of the solid drug matrix is in the range of 2.0-25 grams. In some cases, the solid drug matrix form has a total weight of less than 15 grams; and in some cases, less than 10 grams.

METHOD OF SEDATION: In another aspect, the invention is a method of inducing sedation in a patient in preparation for a clinical procedure. The method could be performed using the liquid composition or the solid matrix formulation described herein. The method comprises simultaneously administering a benzodiazepine (e.g. midazolam) and clonidine to the patient. Any suitable amount of the two active ingredients may be used that, in combination, is sufficient to produce sedation in the patient to allow for the clinical procedure to be performed effectively. This may minimize any adverse psychologic or medical effects associated with the clinical procedure, such as patient anxiety about the procedure, irritability, medical conditions aggravated by stress (such as asthma or epilepsy), behavior problems, reduction in post-operative irritability, or parental separation problems.

In some embodiments, the method induces conscious sedation in the patient. As used herein, 'conscious sedation' means a depressed state of the central nervous system in which the patient is capable of making a purposeful response to verbal or tactile stimulation, is spontaneously breathing, and no intervention is required to maintain a patent airway. This is in contrast to deep sedation in which repeated verbal or painful stimulation is required to get a purposeful response from the patient or spontaneous breathing is inadequate. There are a variety of different ways to assess for the depth of sedation in clinical practice. Examples include the Houpt scale, Ramsay scale, ASA 'Continuum of Sedation' scale, and the 'Modified Observer's Assessment of Alertness/Sedation Scale' (MOASS).

This sedation method could be used in conjunction with any suitable diagnostic or therapeutic clinical procedure. Examples of clinical procedures on which this invention could be used include dental procedures (including oral surgery), radiology procedures, minor surgery procedures, minor wound care procedures, minor orthopedic procedures, emergency medical care, etc. In some embodiments, the method further comprises, after achieving the desired level of sedation in the patient, performing the clinical procedure. That is, the invention can be considered a method of performing the clinical procedure that involves the sedation technique of the invention.

This invention may be particularly useful in children, i.e. pediatric patients. In some embodiments, the patient is a child younger than 16 years age; in some case, younger than 13 years age; and in some case, younger than 11 years age. In some cases, the patient is a child of at least one year age.

In this invention, the dose amount could be stated as the amount of the ingredient drugs given according to the patient's body weight. This could apply to the administration of any of the drug formulations described herein. Clonidine. In some embodiments, the clonidine is administered at a dosage in the range of 1-10 µg/kg (patient body weight); and in some cases, in the range of 2-7 µg/kg (body weight). Midazolam. In some embodiments, the midazolam is administered at a dosage in the range of 0.1-4.0 mg/kg (body weight); and in some cases, in the range of 0.2-2.0 mg/kg.

In some embodiments, the method further comprises simultaneously administering an opioid drug to the patient. Fentanyl. In cases where the drug composition comprises fentanyl, the administered dosage of fentanyl could be in the range of 1.0-20 µg/kg (body weight); and in some cases, in the range of 3.0-10 µg/kg. Meperidine. In cases where the drug composition comprises meperidine, the administered dosage of meperidine could be in the range of 0.5-5.0 mg/kg (body weight); and in some cases, in the range of 1.0-4.0 mg/kg.

There may be a maximum dose that can be given to the patient. For example, the maximum pediatric dose for midazolam may be 20-25 mg; the maximum pediatric dose for clonidine may be 200 µg; the maximum pediatric dose for meperidine may be 100 mg; the maximum pediatric dose for hydroxyzine may be 50 mg. These maximum dose amounts may vary depending on the patient, such as the patient's physical and mental characteristics. Also, maximum dose limitations could apply to the drug compositions or the body weight dosing described above.

The drug composition is administered prior to beginning the clinical procedure. In some embodiments, the drug composition is administered at a time 20-90 minutes prior to beginning the clinical procedure; and in some cases, 30-60 minutes. In some embodiments, the clinical procedure is performed 20-90 minutes after administering the drug composition; and in some cases, 30-60 minutes. In some embodiments, the drug composition is administered at a time 5-60 minutes prior to beginning the clinical procedure; and in some cases, 10-45 minutes. In some embodiments, the clinical procedure is performed 5-60 minutes after administering the drug composition; and in some cases, 10-45 minutes.

In some embodiments, the clinical procedure is performed in a non-hospital setting, such as a clinical practice office, ambulatory care facility, subspecialty procedure suite, free-standing imaging facility, etc. In some embodiments, the clinical procedure is a dental procedure and the sedation is performed by the dental practitioner who is also performing the dental procedure (e.g. dentist, oral surgeon, or clinical assistants therefor). In some embodiments, the sedation is not performed by an anesthesiology specialist (such as an anesthesiologist, nurse anesthetist, or other clinician who is trained or certified in clinical anesthesiology). In some embodiments, the sedation is performed without the presence of an anesthesiology specialist.

In some embodiments, no other sedative agent than the benzodiazepine and the clonidine are given to the patient. That is, the only sedative agents given to the patient are the benzodiazepine and the clonidine. In some embodiments, the patient is not given any opioid drug.

BRIEF DESCRIPTION OF THE DRAWINGS

FIG. 1 shows a multi-dose bottle containing a medicated syrup.

FIG. 2 shows a single-use syringe pre-filled with a medicated syrup.

FIG. 3 shows a medicated lollipop.

FIG. 4 shows a medicated lozenge.

DETAILED DESCRIPTION OF EXAMPLE EMBODIMENTS

Actual working examples of the drug composition were made and tested in a clinical trial setting. First, a medicated syrup formulation was made and clinically tested. Second, a medicated lollipop formulation was made and clinically tested.

Medicated Syrup: The following is an example process that was used make the oral syrup formulation. Make stock preparation of clonidine HCl at 16 µg/ml concentration. Do this by grinding clonidine HCl into fine powder. Mix the powder with 5 ml of flavored sucrose syrup to yield clonidine paste at 16 mg/ml concentration. Further add 100 ml of flavored sucrose syrup to yield clonidine solution at 16 µg/ml concentration. For stock preparation of midazolam, use commercially-available midazolam liquid syrup with midazolam HCl 2.0 mg/ml concentration. Mix the two stock preparations together in an appropriate ratio for the desired drug concentration amounts (e.g. a 1:1 mixing ratio would give 8 µg/ml of clonidine and 2 mg/ml of midazolam.

This medicated syrup was tested in pediatric patients who were undergoing a routine dental procedure, such as tooth extractions, tooth fillings, root canals, and crowns. Prior to beginning the dental procedure, the patients were given the medicated syrup by mouth. The patients were instructed to swallow the medicated syrup. The patient's progress in sedation level was then assessed according to the Houpt scale. When sufficient sedation level was achieved, the dental procedure was started. If sufficient sedation level was not achieved or the sedation was ineffective in allowing the dental procedure to proceed, the study process was terminated for that patient.

Table 1 below summarizes the results of the clinical study. "Time" indicates the wait duration after administering the medicated syrup and beginning the dental procedure. Sedation level is rated mild, moderate (mod), or deep. The patient's Houpt score is also indicated ("abt" means the dental treatment procedure was aborted).

TABLE 1

| | | Clinical Results, Medicated Syrup | | | | |
|---|---|---|---|---|---|---|
| Patient # | Age | Medication, dose per kg weight | Medication, dose amount | Time | Sedation Level | Houpt Score |
| 1 | 3 | clonidine 4 µg/ midazolam 0.5 mg | clonidine 56 µg/ midazolam 7 mg | 30 | mild | 9 |
| 2 | 4 | clonidine 4 µg/ midazolam 0.5 mg | clonidine 89 µg/ midazolam 9.4 mg | 30 | mild | 5 |
| 3 | 5 | clonidine 4 µg/ midazolam 0.5 mg | clonidine 72 µg/ midazolam 9 mg | 50 | mod | 9 |
| 4 | 5 | clonidine 4 µg/ midazolam 0.75 mg | clonidine 90 µg/ midazolam 15 mg | 45 | mild | 7 |
| 5 | 6 | clonidine 4 µg/ midazolam 0.75 mg | clonidine 112 µg/ midazolam 20 mg | 45 | mod | 17 |
| 6 | 5 | clonidine 4 µg/ midazolam 0.75 mg | clonidine 88 µg/ midazolam 16.5 mg | 35 | mild | abt |
| 7 | 2 | clonidine 4 µg/ midazolam 0.75 mg/ hydroxyzine | clonidine 60 µg/ midazolam 11.25 mg/ hydroxyzine 16.25 mg | 45 | mild | abt |
| 8 | 8 | clonidine 4 µg/ midazolam 0.6 mg/ hydroxyzine | clonidine 140 µg/ midazolam 20 mg/ hydroxyzine 77 mg | 45 | mod | 9 |
| 9 | 3 | clonidine 3 µg/ midazolam 0.6 mg/ hydroxyzine | clonidine 53 µg/ midazolam 10.4 mg/ hydroxyzine 18 mg | 47 | mod | 9 |
| 10 | 4 | clonidine 3 µg/ midazolam 0.6 mg/ hydroxyzine | clonidine 64 µg/ midazolam 13 mg/ hydroxyzine 21 mg | 45 | mod | 9 |

TABLE 1-continued

Clinical Results, Medicated Syrup

| Patient # | Age | Medication, dose per kg weight | Medication, dose amount | Time | Sedation Level | Houpt Score |
|---|---|---|---|---|---|---|
| 11 | 4 | clonidine 3 µg/ midazolam 0.6 mg/ hydroxyzine | clonidine 86.7 mg/ midazolam 17.4 mg/ hydroxyzine 27 mg | 45 | mod | 9 |

In patients #3, 8, and 10, sedation was sufficient for the procedure to continue to completion. In the other patients, the level of sedation achieved was not sufficient for the procedure to continue to completion. These cases were likely because of non-optimal compounding technique, which caused formulation instability and non-homogenous distribution of the drugs in the product. This non-homogenous preparation caused a clinically significant variation in drug concentrations. Vital signs were stable in all cases.

Medicated Lollipop: The following is an example process that was used make the lollipop formulation. Make fentanyl citrate into finely ground (trituration) 1% powder mixture by adding fentanyl citrate to a similar particle-size excipient powder material (e.g. steviol glycosides, sugar, etc.) and a similar particle-size food color of choice in a quantity sufficient to make a 1% trituration. Mix with a powder blender (e.g. V-Blender or other pharmaceutical powder blender) to produce a homogenous powder mixture. Obtain an accurate weight from an aliquot. Make clonidine HCl into finely ground (trituration) 1% powder mixture by adding clonidine HCl to a similar particle-size excipient powder material (e.g. steviol glycosides, sugar, etc.) and a similar particle-size food color of choice in a quantity sufficient to make a 1% trituration. Mix with a powder blender (e.g. V-Blender or other pharmaceutical powder blender) to produce a homogenous powder mixture. Obtain an accurate weight from an aliquot. Have ready midazolam HCl powder.

Calculate amount of sorbitol base needed to make 8.0 grams total weight (for each lollipop being made) when combined with all other ingredients (e.g. 7.9 grams of sorbitol base for each lollipop may be the calculated result). Put calculated amount of sorbitol base into a glass beaker and heat to about 160° C. on a hot plate. Optionally, measure water activity and maintain temperature of 160° C. until water activity is below 0.6. This is to ensure that the sorbitol base is anhydrous. Slowly cool the sorbitol base to about 90° C. Put stir bar into beaker and start slow mixing. Add 13.8 mg of the fentanyl 1% triturated powder per each lollipop being made. Add 11 mg of the clonidine 1% triturated powder per each lollipop being made. Add 20.6 mg of the midazolam powder per each lollipop being made. Add 12 mg of steviol glycosides per each lollipop being made. Add 160 µl of stock bubblegum flavor per each lollipop being made. In an alternate processing technique, a rotor-stator homogenizer (instead of a stir bar) could be used for improved homogenization of the mixture and reduction of powder aggregation that can form when adding powders to the base. This forms finely micronized particles and a homogenous mixture (suspension).

Coat metal lollipop molds with a light oil and heat to 90° C. Drain and remove excess oil. Pour the hot 90° C. mixture (of sorbitol base, active pharmaceutical ingredients, and inactive ingredients) into the lollipop molds (or use a 20 ml oral syringe to draw up the mixture and dispense into the molds). After filling the lollipop molds, let cool to room temperature over a 12 hour duration. After cooling, put mold in freezer for about 30 minutes and then remove the medicated lollipops from the mold.

These medicated lollipops were tested in pediatric patients who were undergoing a routine dental procedure, such as tooth extractions, tooth fillings, root canals, and crowns. Prior to beginning the dental procedure, the lollipops were placed into the patient's mouth and dwelled therein for an appropriate wait time. The patient's progress in sedation level was then assessed according to the Houpt scale. When sufficient sedation level was achieved, the dental procedure was started. If sufficient sedation level was not achieved or the sedation was ineffective in allowing the dental procedure to proceed, the study process was terminated for that patient.

Table 2 below summarizes the results of the clinical study. "Time" indicates the wait duration after administering the medicated syrup and beginning the dental procedure. Sedation level is rated mild, moderate (mod), or deep. The patient's Houpt score is also indicated.

TABLE 2

Clinical Results, Medicated Lollipop

| Patient # | Age | Medication, Dose per kg weight | Medication, Dose amount | Time | Sedation Level | Houpt Score |
|---|---|---|---|---|---|---|
| 12 | 6 | clonidine 3.33 µg/ midazolam 0.55 mg/ fentanyl 5.55 µg | clonidine 60 µg/ midazolam 10 mg/ fentanyl 100 µg | 21 | deep | 17 |
| 13 | 6 | clonidine 3.06 µg/ midazolam 0.5 mg/ fentanyl 5 µg | clonidine 60 µg/ midazolam 10 mg/ fentanyl 100 µg | 14 | mod | 15 |
| 14 | 5 | clonidine 2.85 µg/ midazolam 0.48 mg/ fentanyl 4.76 µg | clonidine 60 µg/ midazolam 10 mg/ fentanyl 100 µg | 28 | mod | 13 |
| 15 | 6 | clonidine 2.4 µg/ midazolam 0.4 mg/ fentanyl 4 µg | clonidine 60 µg/ midazolam 10 mg/ fentanyl 100 µg | 27 | mild | 12 |
| 16 | 4 | clonidine 3.4 µg/ midazolam 0.6 mg/ fentanyl 6 µg | clonidine 60 mg/ midazolam 10 mg/ fentanyl 100 µg | 29 | mild | 9 |

TABLE 2-continued

Clinical Results, Medicated Lollipop

| Patient # | Age | Medication, Dose per kg weight | Medication, Dose amount | Time | Sedation Level | Houpt Score |
|---|---|---|---|---|---|---|
| 17 | 3 | clonidine 4.3 μg/ midazolam 0.71 mg/ fentanyl 3.5 μg | clonidine 60 μg/ midazolam 10 mg/ fentanyl 50 μg | 37 | mild | 8 |
| 18 | 3 | clonidine 2.5 μg/ midazolam 0.42 mg/ fentanyl 4.2 μg | clonidine 45 μg/ midazolam 7.5 mg/ fentanyl 75 μg | 42 | mod | 15 |
| 19 | 4 | clonidine 2.75 μg/ midazolam 0.45 mg/ fentanyl 4.6 μg | clonidine 45 μg/ midazolam 7.5 mg/ fentanyl 75 μg | 33 | mild | 8 |
| 20 | 4 | clonidine 3 μg/ midazolam 0.51 mg/ fentanyl 5 μg | clonidine 45 μg/ midazolam 7.5 mg/ fentanyl 75 μg | 20 | mild | 8 |
| 21 | 3 | clonidine 4.1 μg/ midazolam 0.7 mg/ fentanyl 6.9 μg | clonidine 60 μg/ midazolam 10 mg/ fentanyl 100 μg | 35 | mild | 8 |
| 22 | 8 | clonidine 4.12 μg/ midazolam 0.77 μg/ fentanyl 5.15 μg | clonidine 130 mg/ midazolam 24.4 mg/ fentanyl 162.5 μg | 34 | mod | 14 |
| 23 | 5 | clonidine 4.8 μg/ midazolam 0.9 mg/ fentanyl 6 μg | clonidine 90 μg/ midazolam 16.9 mg/ fentanyl 113 μg | 15 | mod | 15 |
| 24 | 8 | clonidine 4.24 μg/ midazolam 0.8 mg/ fentanyl 5.3 μg | clonidine 110 μg/ midazolam 21 mg/ fentanyl 138 μg | 25 | mod | 13 |
| 25 | 5 | clonidine 4 μg/ midazolam 0.75 mg/ fentanyl 5 μg | clonidine 70 μg/ midazolam 13.1 mg/ fentanyl 87.5 μg | 22 | mild | 8 |
| 26 | 3 | clonidine 4.4 μg/ midazolam 0.83 mg/ fentanyl 5.5 μg | clonidine 70 μg/ midazolam 13.1 mg/ fentanyl 87.5 μg | 24 | mild | 7 |
| 27 | 7 | clonidine 4.9 μg/ midazolam 0.92 mg/ fentanyl 5.2 μg | clonidine 130 μg/ midazolam 24.4 mg/ fentanyl 138 μg | 37 | mod | 17 |
| 28 | 8 | clonidine 4.24 μg/ midazolam 0.8 μg/ fentanyl 5.3 μg | clonidine 110 μg/ midazolam 20.6 mg/ fentanyl 138 μg | 21 | mod | 13 |
| 29 | 6 | clonidine 5.5 μg/ midazolam 0.96 mg/ fentanyl 6.8 μg | clonidine 110 μg/ midazolam 20.6 mg/ fentanyl 138 μg | 22 | mod | 16 |
| 30 | 3 | clonidine 6 μg/ midazolam 1.13 mg/ fentanyl 7.55 μg | clonidine 90 μg/ midazolam 17 mg/ fentanyl 113 μg | 24 | mod | 16 |
| 31 | 3 | clonidine 5.3 μg/ midazolam 0.99 μg/ fentanyl 6.6 μg | clonidine 90 μg/ midazolam 17 mg/ fentanyl 113 μg | 25 | mild | 8 |
| 32 | 5 | clonidine 4.2 μg/ midazolam 0.79 mg/ fentanyl 5.2 μg | clonidine 90 μg/ midazolam 17 mg/ fentanyl 113 μg | 30 | mild | 8 |
| 33 | 6 | clonidine 4.95 μg/ midazolam 0.93 mg/ fentanyl 6.2 μg | clonidine 110 μg/ midazolam 20.6 mg/ fentanyl 138 μg | 16 | mod | 16 |
| 34 | 4 | clonidine 4.7 μg/ midazolam 0.88 mg/ fentanyl 5.9 μg | clonidine 90 μg/ midazolam 17 mg/ fentanyl 113 μg | 23 | mild | 6 |
| 35 | 9 | clonidine 4.2 μg/ midazolam 0.8 mg/ fentanyl 4.4 μg | clonidine 130 mg/ midazolam 24.4 mg/ fentanyl 138 μg | 36 | mild | 7 |
| 36 | 6 | clonidine 5.3 μg/ midazolam 1 mg/ fentanyl 6.6 μg | clonidine 110 μg/ midazolam 20.6 mg/ fentanyl 138 μg | 38 | mild | 9 |
| 37 | 4 | clonidine 4.4 μg/ midazolam 0.83 mg/ fentanyl 5.5 μg | clonidine 70 μg/ midazolam 13.1 mg/ fentanyl 87.5 μg | 21 | mild | 6 |
| 38 | 3 | clonidine 4.6 μg/ midazolam 0.87 mg/ fentanyl 5.7 μg | clonidine 90 μg/ midazolam 17 mg/ fentanyl 113 μg | 35 | mod/deep | 17 |

There was 100% compliance with the child accepting the lollipop. Notably, this is higher than the compliance rate for oral medications that are swallowed. Parental separation was excellent except in patients #16, 29, and 31. In patients #12-15, 18, 22-24, 27, 28, 30, 33, and 38, sedation was sufficient for the procedure to continue to completion. In the other patients, the level of sedation achieved was not sufficient for the procedure to continue to completion. In all cases, vital signs were stable and the patient had no memory of the procedure (amnesia).

Compared to opioid drugs, benzodiazepines (such as midazolam) have a much better safety profile. Thus, being able to reduce the amount of fentanyl is an important benefit. Through synergistic effect with the clonidine and midazolam, the lollipops were able provide effective sedation despite having a reduced amount of fentanyl compared to the ACTIQ® lollipop product.

Product Examples: Shown in the drawings are some examples of drug product forms in which this invention may be implemented. FIG. 1 shows a multi-dose bottle 10 containing a medicated syrup. There is a spoon 12 for orally administering the doses from the bottle 10. The patient swallows the medicated syrup. FIG. 2 shows a single-use syringe 20 pre-filled with a medicated syrup. The dispensing spout is closed with a cap 22. In use, cap 22 is removed and the contents of syringe 20 is squirted into the patient's mouth. The patient swallows the medicated syrup. FIG. 3 shows a medicated lollipop 30 on a stick 32. The patient puts the lollipop 30 in their mouth and lets it dwell therein for transmucosal absorption. FIG. 4 shows a medicated lozenge 40. The patient puts the lozenge 40 in their mouth and lets it dwell therein for transmucosal absorption.

The descriptions and examples given herein are intended merely to illustrate the invention and are not intended to be limiting. Each of the disclosed aspects and embodiments of the invention may be considered individually or in combination with other aspects, embodiments, and variations of the invention. In addition, unless otherwise specified, the steps of the methods of the invention are not confined to any particular order of performance. Modifications of the disclosed embodiments incorporating the spirit and substance of the invention may occur to persons skilled in the art, and such modifications are within the scope of the invention.

Any use of the word "or" herein is intended to be inclusive and is equivalent to the expression "and/or," unless the context clearly dictates otherwise. As such, for example, the expression "A or B" means A, or B, or both A and B. Similarly, for example, the expression "A, B, or C" means A, or B, or C, or any combination thereof.

The invention claimed is:

1. A solid drug matrix formulation comprising:
   clonidine in an amount ranging from 10-300 µg;
   midazolam in an amount ranging from 1-40 mg;
   fentanyl in an amount ranging from 10-300 µg.
2. The drug formulation of claim 1, wherein the amount of fentanyl is at least 10 µg, but less than 190 µg.
3. The drug formulation of claim 2, wherein the amount of fentanyl is at least 10 µg, but less than 175 µg.
4. The drug formulation of claim 3, wherein the amount of fentanyl is at least 10 µg, but less than 150 µg.
5. The drug formulation of claim 1, being in the form of a lozenge or lollipop.
6. The drug formulation of claim 1, having a size of at least 1.0 cm along its widest dimension.
7. The drug formulation of claim 6, having a size of at least 1.5 cm along its widest dimension.
8. The drug formulation of claim 6, having a size of at least 1.0 cm, but less than 3.5 cm along its widest dimension.
9. The drug formulation of claim 1, having a total weight in the range of 2.0-25 grams.
10. The drug formulation of claim 9, having a total weight of at least 2.0 grams, but less than 15 grams.
11. The drug formulation of claim 10, having a total weight of at least 2.0 grams, but less than 10 grams.
12. The drug formulation of claim 1, further comprising a sweetener or flavor enhancer.
13. A method of inducing sedation in a patient, comprising:
    having a solid drug matrix formulation of claim 1;
    administering the solid drug matrix formulation to the patient orally and letting dwell in patient's mouth for a duration of time;
    allowing time for transmucosal absorption of the clonidine, midazolam, and fentanyl in the patient's mouth.
14. The method of claim 13, wherein the time allowed for transmucosal absorption is 5-60 minutes duration.
15. The method of claim 14, wherein the time allowed for transmucosal absorption is 10-45 minutes duration.
16. The method of claim 13, wherein the sedation is in preparation for a clinical procedure.
17. The method of claim 16, wherein the clinical procedure is performed after waiting a duration of 10-45 minutes duration from administering the solid drug matrix formulation to the patient.
18. The method of claim 16, wherein the sedation and the clinical procedure are performed together in a non-hospital setting.
19. The method of claim 16, wherein the clinical procedure is a dental procedure and the sedation is performed by a dental practitioner who is also performing the dental procedure.
20. The method of claim 16, wherein the sedation is not performed by an anesthesiology specialist.

* * * * *